(12) United States Patent
Higo

(10) Patent No.: US 6,603,320 B2
(45) Date of Patent: Aug. 5, 2003

(54) ELECTRIC CONDUCTOMETER, ELECTRODE FOR MEASURING ELECTRIC CONDUCTIVITY, AND METHOD FOR PRODUCING THE SAME

(75) Inventor: Yuji Higo, Tokyo (JP)

(73) Assignee: Organo Corporation, Tokyo (JP)

( * ) Notice: Subject to any disclaimer, the term of this patent is extended or adjusted under 35 U.S.C. 154(b) by 0 days.

(21) Appl. No.: 09/937,940

(22) PCT Filed: Feb. 2, 2001

(86) PCT No.: PCT/JP01/00765
§ 371 (c)(1),
(2), (4) Date: Oct. 2, 2001

(87) PCT Pub. No.: WO01/59441
PCT Pub. Date: Aug. 16, 2001

(65) Prior Publication Data
US 2002/0153908 A1 Oct. 24, 2002

(30) Foreign Application Priority Data
Feb. 7, 2000 (JP) .......................................... 2000-28983

(51) Int. Cl.[7] .............................................. G01R 27/08
(52) U.S. Cl. ....................................... 324/702; 324/691
(58) Field of Search ................................ 324/649, 658, 324/690, 688, 693, 700, 702, 691; 372/87; 436/133; 210/192, 748

(56) References Cited

U.S. PATENT DOCUMENTS 4,956,847 A * 9/1990 Terai et al. .................... 372/87
5,275,957 A * 1/1994 Blades et al. ................ 436/133
5,951,859 A * 9/1999 Miura et al. ................. 210/192
6,156,211 A * 12/2000 Gonzalez-Martin et al. 210/748
6,238,630 B1 * 5/2001 Iimura ..................... 422/186.3

FOREIGN PATENT DOCUMENTS

| JP | 8-278270 A | 10/1996 |
| JP | 9-89827 A | 4/1997 |
| JP | 9-228022 | 9/1997 |
| JP | 9-262466 A | 10/1997 |
| JP | 10-18083 A | 1/1998 |
| JP | 11-198633 A | 7/1999 |

* cited by examiner

Primary Examiner—N. Le
Assistant Examiner—Donald M Lair
(74) Attorney, Agent, or Firm—Norris McLaughlin & Marcus

(57) ABSTRACT

An electric conductometer comprising at least two electric conductivity measuring electrodes each body of which is made from a conductive metal and each surface of which is formed by a titanium oxide layer as an electrode surface, a space for storing a substance to be measured formed between the electrode surfaces of the electrodes, and means for irradiating light to the electrode surfaces. Since the electrode surfaces are formed from the titanium oxide layers, organic substances contained in a measuring system are decomposed and prevented automatically from adhering or being adsorbed to the electrode surfaces. Consequently, electric conductivity can be measured stably and accurately at all times without substantially requiring any cleaning.

4 Claims, 3 Drawing Sheets

ELECTRIC CONDUCTOMETER, ELECTRODE FOR MEASURING ELECTRIC CONDUCTIVITY, AND METHOD FOR PRODUCING THE SAME

This application is a 371 of PCT JP01/00765, filed on Feb. 2, 2001.

TECHNICAL FIELD OF THE INVENTION

The present invention relates to an electric conductometer, and an electrode for measuring electric conductivity and a method for producing the same, and specifically, relates to an apparatus capable of measuring electric conductivity accurately and stably, at a good repeatability substantially without requiring any cleaning of the electrode surface, and a method for producing the same.

BACKGROUND ART OF THE INVENTION

Electric conductivity is especially employed as a scale to measure a concentration of ions capable of migrating in an aqueous solution, and an electric conductometer is employed to measure ion concentrations in many kinds of aqueous solutions. The electric conductometer has usually at least two electrodes, and the electric conductivity or resistance of an aqueous solution present between the electrodes is determined by measuring the electric current or voltage between at least two electrodes in contact with the aqueous solution.

The electrode of this electric conductometer is constructed usually from an oxidation and corrosion resistant conductive metal such as platinum black comprising fine particles of platinum, simply platinum, platinum or gold plated conductive metals, or stainless steel, in order not to be oxidized even when the electrode comes into contact with an aqueous solution, and in order to ensure stability of the measurement by setting an area of the electrode to be broad.

In such an electric conductometer, an electrode surface is usually cleaned regularly to perform an accurate measurement. Because many organic substances are generally contained in an aqueous solution to be measured, and are adhered or adsorbed onto an electrode surface, the adhered nonconductive organic substances heighten the resistance at the electrode surface, and the increase in the resistance may make an accurate measurement impossible, this electrode surface is regularly cleaned to avoid such inconvenience. Such adhesion or adsorption of organic substances has been considered to be an unavoidable phenomenon in a conventional apparatus, because of the measurement principle of an electric conductometer, that is, wherein ion exchange is performed on an electrode surface.

In other words, in a measurement of electric conductivity, because an electric current flows in a measurement system more or less, and the strength of the current is to be measured, a conductive electrode, namely, an electrode made from a conductive metal is inevitably used. Therefore, in an electrode surface made from a conductive metal, when ion exchange is performed by energization, nonconductive organic substances are adhered or adsorbed onto the electrode surface. When such adhesion or adsorption of the organic substances occurs, the resistance increases and an aimed electrode surface for measurement cannot be formed, and as a result, the measurement accuracy is sacrificed or a measurement repeatability is lost. Therefore, frequent cleanings of the electrode surface are required to avoid such an inconvenience.

DISCLOSURE OF THE INVENTION

Accordingly, it is an object of the present invention to provide an electric conductometer, which can automatically prevent organic substances contained in a measuring system from adhering or being adsorbed onto an electrode surface, and which can measure an electric conductivity stably and accurately at all times substantially without requiring any cleaning, and an electrode for measuring the electric conductivity and a method for producing the same.

To accomplish the above-described object, an electrode for measuring electric conductivity according to the present invention is characterized in that an electrode surface is formed by a titanium oxide layer on a surface of an electrode body made from a conductive metal.

Further, an electric conductometer according to the present invention comprises at least two electric conductivity measuring electrodes each body of which is made from a conductive metal and each surface of which is formed by a titanium oxide layer as an electrode surface, a space for storing a substance to be measured formed between the electrode surfaces of the electric conductivity measuring electrodes, and means for irradiating light to the electrode surfaces. A substance to be measured is generally an aqueous solution, but a gaseous substance or slurry-like substance can also be measured.

In this electric conductometer, it is preferred that light irradiated by the above-described means for irradiating light has a wavelength which brings about a photocatalyst activity of the above-described titanium oxide layer. For example, light with a wavelength from about 300 to about 400 nm can be employed. As means for irradiating light, a light source composed of means for irradiating ultraviolet rays and the like such as a black light may be directly employed, and a light guiding material (for example, an optical fiber or a tube and the like comprising a light guiding raw material) to guide light from a light source provided as means for irradiating light may be also employed. Further, the light from a light guiding material may be added to light irradiated directly from a light source.

Further, the above-described space for storing a substance to be measured may be defined by a light transmitting material, and it may be constituted so that the light from means for irradiating light is irradiated onto an electrode surface through the light transmitting material (for example, glass). In this case, if a titanium oxide coating layer capable of transmitting light is provided on a surface (a surface in contact with solution) of the side of the space for storing a substance to be measured (made of light transmitting material), adhesion of organic matters and the like to this surface of the light transmitting material can be prevented by super-hydrophilicity and decomposition property of organic substances ascribed to the titanium oxide layer.

Further, the aforementioned electric conductivity measuring electrode according to the present invention can be produced by the following method. Namely, a method for producing an electric conductivity measuring electrode according to the present invention is characterized in that an electrode surface is formed by providing a titanium oxide layer on a surface of an electrode body made from a conductive metal by sputtering or plating. Alternatively, a method can also be employed wherein an electrode surface made from a titanium oxide layer is formed by providing oxygen to a surface of an electrode body made from a titanium metal. As the method for forming a titanium oxide layer by providing oxygen, a method based on air oxidation other than a method utilizing electrolysis can be employed.

In the above-described electric conductivity measuring electrode and electric conductometer using the same according to the present invention, since the titanium oxide layer is formed on the surface of the electrode body made from a conductive metal, a photocatalyst activity of the titanium oxide is exhibited by irradiating light with an appropriate wavelength (for example, an ultraviolet ray) to the layer, organic substances in contact with the titanium oxide layer or existing nearby the layer in water are decomposed, and adhesion or adsorption thereof to the titanium oxide layer is automatically prevented. Therefore, it is not necessary to clean this electrode surface regularly, and the electrode surface is always maintained at a desirable surface condition without adhesion or adsorption of the organic substances, and an area of the electrode with such a desirable surface condition may be also maintained at an initial condition at all times. As a result, electric conductivity can be measured stably and accurately at all times, and repeatability of the accuracy of the measurement can be ensured with no problems.

Furthermore, according to the method for producing an electrode for measuring electric conductivity according to the present invention, the above-described electrode suitable for measurement of electric conductivity can be manufactured easily and inexpensively.

THE BEST MODE FOR CARRYING OUT THE INVENTION

Hereinafter, desirable embodiments of the present invention will be explained referring to figures.

Figure 1:
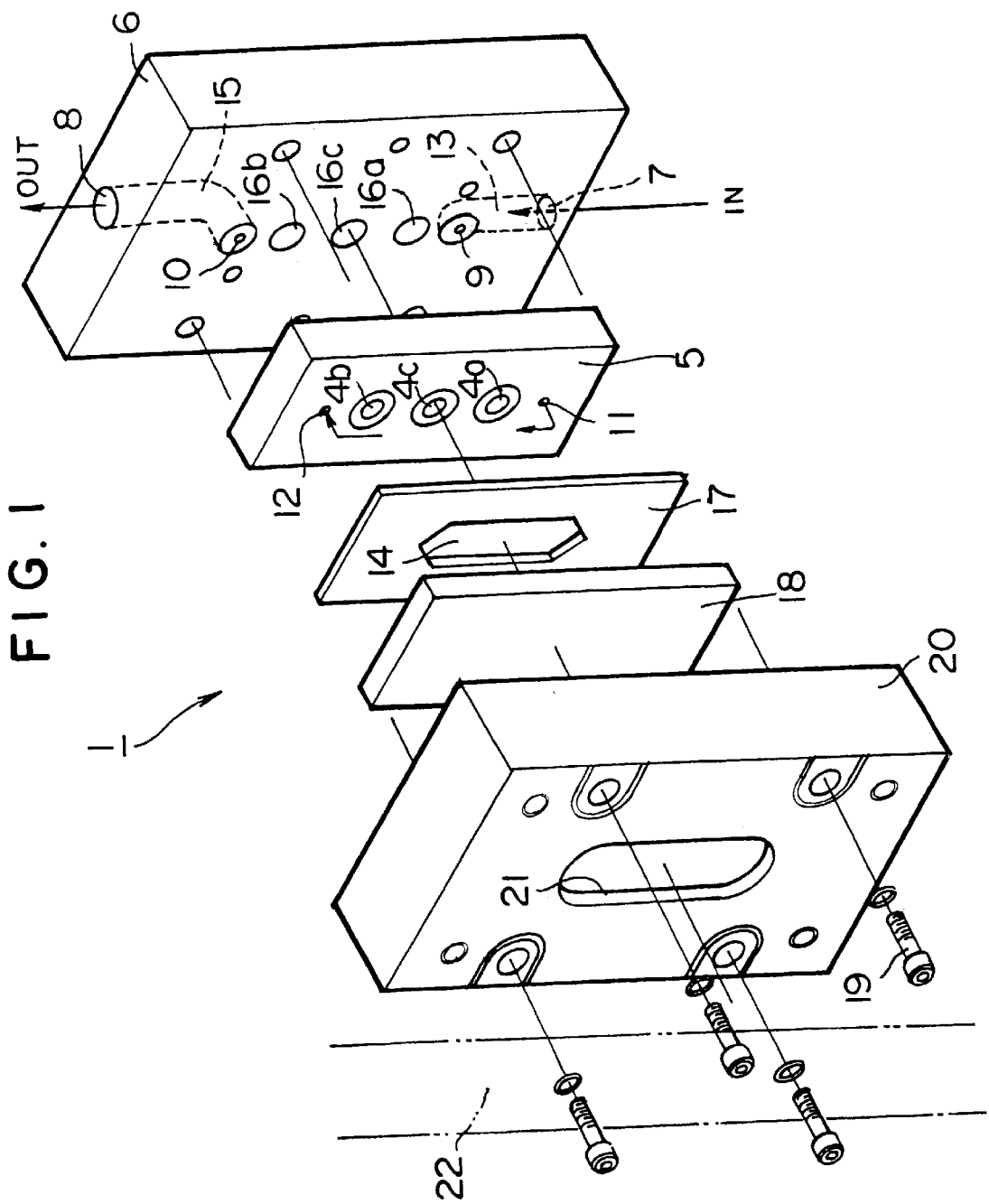
FIG. 1 is an exploded perspective view of an electric conductometer according to a first embodiment of the present invention.
Figure 2:
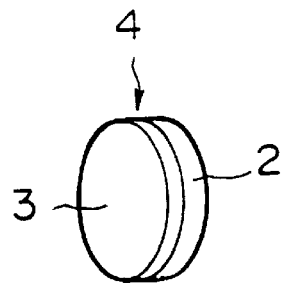
FIG. 2 is an enlarged perspective view of an electric conductivity measuring electrode of the apparatus depicted in FIG. 1.

FIG. 1 shows an electric conductometer according to a first embodiment of the present invention. In this electric conductometer 1, an electric conductivity measuring electrode 4 wherein an electrode surface is formed by a titanium oxide layer 3 on a surface of an electrode body 2 made from a conductive metal, shown in FIG. 2, is employed. The titanium oxide layer 3 is formed by a surface treatment of sputtering or plating and the like, or is formed by oxidizing the surface of the electrode body 2 made from a titanium metal. The oxidation is conducted by electrolysis or air oxidation.

Three electric conductivity measuring electrodes 4 are used in this embodiment, and are attached to an electrode holder 5 comprising an insulation material, in a condition where the electrode surfaces are exposed, as shown in FIG. 1. Three electrodes 4 are disposed in a raw, and the electrodes 4a and 4b at both sides constitute power supplying electrodes connected to a power source, and the electrode 4c at the center position constitutes a detecting electrode functioning as a sensor for detecting electric conductivity.

Electrode holder 5 is fixed at a predetermined position of a substrate 6. In the substrate 6, inlet 7 for introducing a fluid to be measured (for example, an aqueous solution), outlet 8 for discharging the fluid, and flow holes 9 and 10 for measuring electric conductivity are provided. In the electrode holder 5, flow holes 11 and 12 are provided, and the flow hole 11 is disposed to communicate with the flow hole 9 of the substrate and the flow hole 12 is disposed to communicate with flow hole 10 of the substrate, respectively. A fluid to be measured introduced from inlet 7 is sent into a space 14 for storing a substance to be measured, which is defined on the side of the electrode surfaces of the respective electrodes 4, through an inside path 13 of substrate 6, the flow hole 9, and the flow hole 11 of electrode holder 5. The space 14 for storing a substance to be measured forms a flow path for measuring electric conductivity of the fluid to be measured. The fluid from the space 14 for storing a substance to be measured is discharged from outlet 8 through the flow hole 12 of electrode holder 5, the flow hole 10 of substrate 6, and an inside path 15.

In the substrate 6, through holes 16a, 16b, 16c are opened at positions corresponding to the respective electrodes 4a, 4b, 4c, and necessary electric wires are pulled out of the through holes 16a, 16b, 16c.

The space 14 for storing a substance to be measured, in this embodiment, is defined by a sheet-like packing 17, and a transparent glass plate 18 provided as a light transmitting material which is disposed to confront electrode holder 5 with a gap via packing 17. It is preferred that a titanium oxide coating layer is provided at a degree, that the light transmitting property is not damaged, also to the surface of glass plate 18 on its side facing the space 14 for storing a substance to be measured. The electric conductivity of the fluid, flowing in this space 14 for storing a substance to be measured, is measured.

Electrode holder 5, packing 17 and glass plate 18 are fixed to a cover body 20 on one surface side of substrate 6 by bolts 19. A window 21 for transmitting light is opened on cover body 20. Through this window 21, light from means for irradiating light 22 which is disposed outside is irradiated. Light irradiated is shed on titanium oxide layers 3 that form the electrode surfaces of the respective electrodes 4a, 4b, 4c through glass plate 18 from the window 21. Light having a wavelength that brings about a photocatalyst activity to titanium oxide layers 3 is selected as the light to be irradiated. For example, an ultraviolet ray with a specified wavelength (for example, a wavelength of from 300 to 400 nm) can be employed, and as means for irradiating light 22, for example, a black light that irradiates ultraviolet rays can be used.

In the electric conductometer 1 according to the first embodiment constituted as described above, by irradiating light from means for irradiating light 22, titanium oxide layers 3 provided on the surfaces of the respective electrodes 4a, 4b, 4c exhibit photocatalyst activity, and even when organic substances are contained in a fluid to be measured flowing through the space 14 for storing a substance to be measured, the organic substances are decomposed by the photocatalyst activity. Therefore, when measuring electric conductivity, even if ion exchange is performed on the electrode surfaces, the nonconductive organic substances are prevented from adhering or being adsorbed onto the electrode surfaces. As a result, regular cleaning of an electrode surface, that has been conducted, is not required any longer, and electric conductivity can be measured stably and accurately at all times without cleaning. Further, repeatability of such a high-accuracy measurement can be also ensured.

Further, if a titanium oxide coating layer is provided on the surface of glass plate 18 on its side facing the space 14 for storing a substance to be measured, the adhesion or adsorption of organic substances to this surface side is also prevented, and accumulation of the organic matters in the space 14 for storing a substance to be measured is prevented, thereby maintaining the high-accuracy measurement.

To confirm an effect due to the photocatalyst activity by titanium oxide layer 3 in electric conductometer 1 shown in FIG. 1, examinations 1 and 2 were carried out as follows.

Examination 1

To a solution containing 10 ppm sodium acrylate were added sodium sulfate and sulfuric acid to prepare a solution with a conductivity of about 1000 $\mu$S. A pump connected with a degasifier was connected to an inlet side of the electric conductometer shown in FIG. 1, and the fluid described above was fed at a flow rate of 0.5 ml/min. A measured value of the electric conductometer connected was cramped to zero point, and the sensitivity was adjusted by increasing the measuring range. The sensitivity was adjusted to level 2 at 10 micro-measuring range (a range of the recorder was adjusted so as to be 5 $\mu$S of its full span at 1 volt), and the examination was started. When a black light of ultraviolet rays was used as means for irradiating light 22 and the measurement was continued by recording at a condition of stopping the pump while continuing the irradiation by the black light, an increase of electric conductivity of 0.24 $\mu$S in 1 hour was observed. Then, the pump was operated again, the black light was turned off, and after 15 minutes the pump was stopped and the recording was continued by a recorder. Any increase in the electric conductivity could not be observed for 1 hour. From this result, it is understood that, when the photocatalyst activity was exhibited by irradiating light on the titanium oxide layer of the electrode, polyacryl acid was decomposed by the titanium oxide of the electrode surface, and electric conductivity was increased. On the other hand, when the light was turned off, it is understood that the photocatalyst activity was not exhibited, decomposition on the electrode surface did not occur, and the electric conductivity did not change.

Examination 2

Using the same solution as that of Examination 1, the flow rate of the solution passing through the electric conductometer during the light turning-on condition was changed, and an increase degree of the electric conductivity was measured under the same condition as that of Examination 1. When an electric conductivity at a flow rate of 1 ml/min. was taken as a reference value, an increase in electric conductivity of 0.12 $\mu$S was observed when the flow rate was 0.1 ml/min. When the flow rate was further decreased down to 0.05 ml/min., an increase in electric conductivity of 0.21 $\mu$S, which was approximately two times the above-described valve, was observed. Even in this Examination 2, organic substances were decomposed on the titanium oxide layer of the electrode surface, an increase of electric conductivity was observed, and an effect due to the photocatalyst activity was observed.

Figure 3:
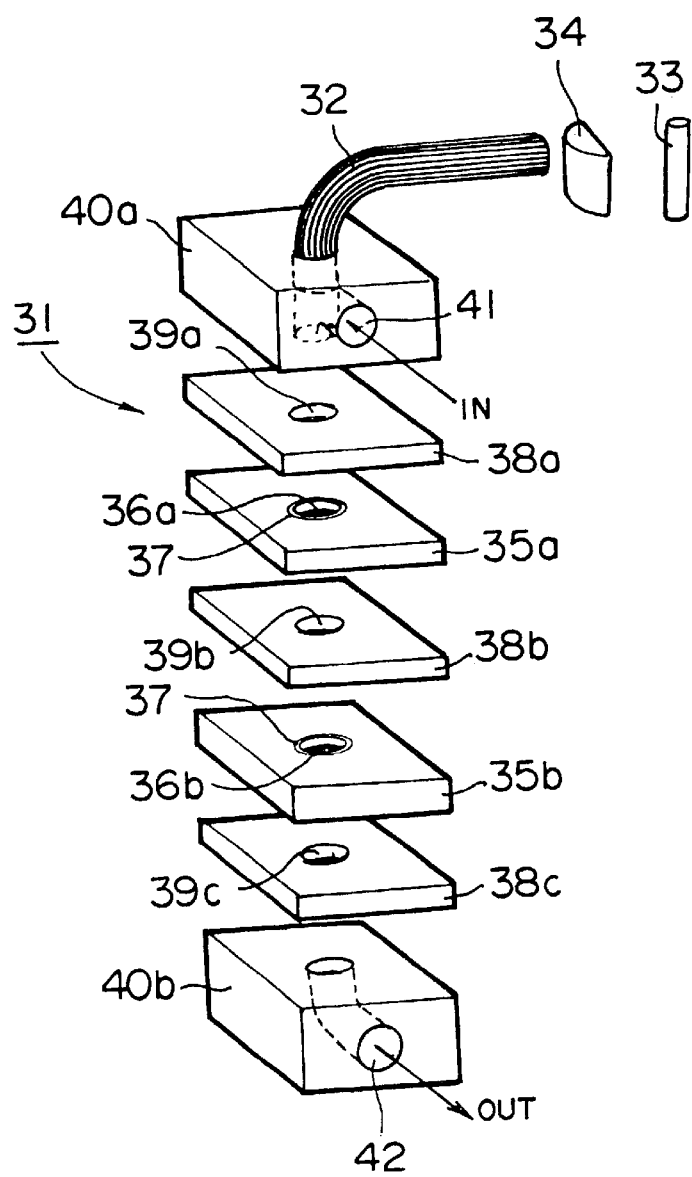
FIG. 3 is an exploded perspective view of an electric conductometer according to a second embodiment of the present invention.

FIG. 3 shows an electric conductoneter 31 according to a second embodiment of the present invention. In this embodiment, an optical fiber forming a light guiding material is used as means for irradiating light. Black light 33 of ultraviolet rays is used as a light source, light converged by a dome-type converging lens 34 is irradiated onto an incident end of an optical fiber 32, and the light guided in the optical fiber 32 is emitted from an emitting end of the optical fiber on the opposite side.

In this embodiment, plate-like electrode bodies 35a, 35b are composed of a titanium metal, and titanium oxide layers 37 are formed on the inner circumferential surfaces of holes 36a, 36b opened in the central portion. The electrode bodies 35a, 35b are isolated by being sandwiched between isolation sheets 38a, 38b, and 38c having, respectively, holes 39a, 39b, and 39c in the central portions, and an electric current for measuring electric conductivity flows between the electrode bodies 35a and 35b.

A stacked body comprising these electrode bodies 35a, 35b and isolation sheets 38a, 38b, 38c is sandwiched by holders 40a, 40b from both sides. A space for storing a substance to be measured for measuring electric conductivity of a fluid to be measured is defined by holes 36a, 36b of electrode bodies 35a, 35b and holes 39a, 39b, 39c of isolation sheets 38a, 38b, 38c. Into the holder 40a, an emitting end of an optical fiber 32 is inserted at a sealed condition, and light may be irradiated toward the space for storing a substance to be measured wherefrom. The fluid to be measured introduced from inlet 41 of holder 40a is discharged from outlet 42 of holder 40b through the space for storing a substance to be measured.

In the embodiment described above, although light is irradiated only from the side of one holder 40a via optical fiber 32, when a space for storing a substance to be measured is relatively long, light may be guided also from the side of holder 40b at the opposite side.

Thus, with respect to disposition of a conductive metal, disposition of a titanium oxide layer of an electrode surface, and constitution of a space for storing a substance to be measured in the electric conductometer can be designed to an arbitrary formation.

Figure 4:
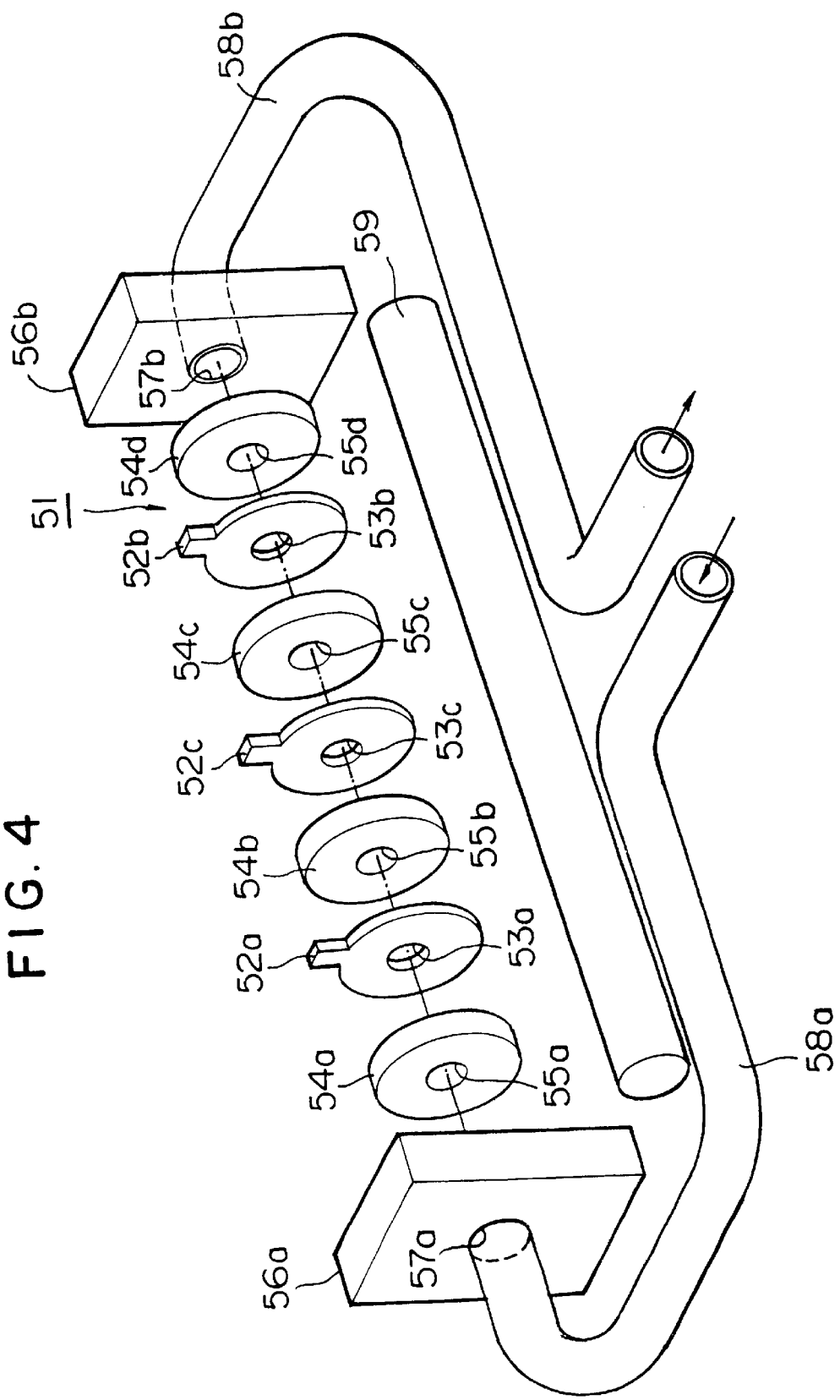
FIG. 4 is an exploded perspective view of an electric conductometer according to a third embodiment of the present invention.

FIG. 4 shows an electric conductometer 51 according to a third embodiment of the present invention. In this embodiment, three electrodes 52a, 52b, 52c are provided, and for example, the electrodes 52a,52b on both sides are constituted as power supplying electrodes connected to a power source, and the electrode 52c disposed between them is constituted as a detecting electrode functioning as a sensor for detecting an electric conductivity. Through holes 53a, 53b, 53c are opened in the central portions of the respective electrode 52a, 52b, 52c, and a titanium oxide layer is provided on an inner surface of each of the holes 53a, 53b, 53c. Spacers 54a, 54b, 54c, 54d made from a light transmitting isolation material (for example, 4 fluoride-ethylene) are disposed on both sides of the respective electrodes 52a, 52b, 52c, and the respective electrodes and spacers are stacked alternately. Through holes 55a, 55b, 55c, 55d are opened in the central portions of the respective spacers 54a, 54b, 54c, 54d. Support materials 56a, 56b are disposed outside of the spacers 54a, 54d at both sides, and a stacked body comprising the electrodes 52a, 52b, 52c and the spacers 54a, 54b, 54c, 54d is sandwiched from both sides by the support materials. Through holes 57a, 57b are opened also in the central portions of the respective support materials 56a, 56b, and in the holes 57a, 57b, one end of a tube 58a for introducing a fluid to be measured and one end of a tube 58b for discharging the fluid are inserted and fixed, respectively.

A flow path of a fluid to be measured is defined by holes 55a, 53a, 55b, 53c, 55c, 53b, 55d connected by stacking the electrodes 52a, 52b, 52c and the spacers 54a, 54b, 54c, 54d. A fluid to be measured introduced through tube 58a is discharged through tube 58b, after flowing in the inside of this flow path. These tubes 58a, 58b are composed of a light transmitting material (for example, 4 fluoride-ethylene), and an ultraviolet ray with a predetermined wavelength is irradiated from black light 59 provided as means for irradiating light. As the ultraviolet ray irradiated repeats diffusion and reflection in tubes 58a, 58b as well as transmits the tubes, the ultraviolet ray is guided along the tubes 58a, 58b, and guided to an inner surface comprising a titanium oxide layer in each of electrodes 52a, 52b, 52c from the portions of holes 57a, 57b at both sides. Further, as the respective spacers 54a, 54b, 54c, 54d are also composed of a light transmitting material, the ultraviolet ray from black light 59 is irradiated to the inner surfaces of electrodes 52a, 52b, 52c after transmitting each spacer while performing diffusion and reflection. Especially, by forming each electrode and spacer to be relatively thin (for example, the thickness of each electrode is about 0.2 mm, and the thickness of each spacer is about 1 mm), because a flow path defined by each electrode and each spacer becomes relatively short, even if a particular light transmitting material such as an optical fiber is not used, a sufficient amount of light for measurement is irradiated onto an electrode surface by the light guiding along light transmitting tubes 58a, 58b as described above, and by the light guiding through light transmitting spacers 54a, 54b, 54c, 54d. Therefore, in this embodiment, a simpler and smaller unit can be constructed.

INDUSTRIAL APPLICATION OF THE INVENTION

In the electric conductometer according to the present invention, since an electrode surface is formed from a titanium oxide layer, organic substances contained in a measuring system are decomposed and prevented automatically from adhering or being adsorbed to the electrode surface, and therefore, electric conductivity can be measured stably and accurately at all times substantially without requiring any cleaning. Therefore, the electric conductometer according to the present invention can be applied for any field that requires a high-accuracy measurement of electric conductivity, for example, it can be applied suitably to any kind of water treatment system, sludge treatment system or gaseous system and the like.

What is claimed is:

1. An electric conductometer comprising:
   a) at least two electric conductivity measuring electrodes, each of said at least two electric conductivity measuring electrodes having a body which is made from a conductive metal, and each of said at least two electric conductivity measuring electrodes having an electrode surface which is formed by a titanium oxide layer as an electrode surface,
   b) a space for storing a substance to be measured formed between the electrode surfaces of said at least o electric conductivity measuring electrodes, wherein said space is defined by a light transmitting material, and a titanium oxide coating layer capable of transmitting light is provided on a surface of said light transmitting material, and
   c) means for irradiating light to the electrode surfaces, wherein light from said means for irradiating light is irradiated onto said electrode surfaces through said light transmitting material.

2. The electric conductometer according to claim 1, wherein light irradiated from said light irradiating means has a wavelength which brings about a photocatalyst activity of said titanium oxide layer.

3. The electric conductometer according to claim 1, wherein said light irradiating means comprises a light source.

4. The electric conductometer according to claim 1, wherein said light irradiating means comprises a light guiding material which guides light from a light source.

* * * * *

UNITED STATES PATENT AND TRADEMARK OFFICE
CERTIFICATE OF CORRECTION

PATENT NO. : 6,603,320 B2
DATED : August 5, 2003
INVENTOR(S) : Higo

It is certified that error appears in the above-identified patent and that said Letters Patent is hereby corrected as shown below:

Column 8,
Line 14, "at least o" should read -- at least two --

Signed and Sealed this

Eighth Day of March, 2005

JON W. DUDAS
*Director of the United States Patent and Trademark Office*